United States Patent [19]

Araki et al.

[11] Patent Number: 4,681,979

[45] Date of Patent: Jul. 21, 1987

[54] METHOD FOR PRODUCING COMPOUNDS HAVING A DOUBLE BOND AT THE TERMINAL

[75] Inventors: Masashi Araki, Takatsuki; Takuo Hibi, Ichihara, both of Japan

[73] Assignee: Sumitomo Chemical Company, Ltd., Osaka, Japan

[21] Appl. No.: 925,920

[22] Filed: Nov. 3, 1986

[30] Foreign Application Priority Data

Nov. 11, 1985 [JP] Japan .................................. 60-252574

[51] Int. Cl.⁴ ................................................. C07C 1/24
[52] U.S. Cl. ..................................... 585/640; 585/639
[58] Field of Search ................ 585/638, 639, 640, 651

[56] References Cited

U.S. PATENT DOCUMENTS 4,490,567 12/1984 Drake .................................. 585/640

FOREIGN PATENT DOCUMENTS 1000026 1/1986 Japan .................................... 585/640
1233020 5/1971 United Kingdom ................ 585/640
279613 3/1969 U.S.S.R. .............................. 585/640

OTHER PUBLICATIONS

Chemical Abstract, vol. 105: 138521p.
Davis et al., Ind. Eng. Chem. Prod. Res. Dev., vol. 18, 191–198 (1979).

*Primary Examiner*—Asok Pal
*Attorney, Agent, or Firm*—Stevens, Davis, Miller & Mosher

[57] ABSTRACT

A method for producing a compound having a double bond at an end of the molecule, comprising the dehydrating reaction of a compound represented by the general formula

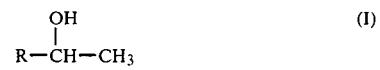

wherein R is a $C_2$–$C_{20}$ hydrogen group having optionally double bonds, in the presence of a zirconium oxide catalyst treated with alkali solution.

11 Claims, No Drawings

METHOD FOR PRODUCING COMPOUNDS HAVING A DOUBLE BOND AT THE TERMINAL

BACKGROUND OF THE INVENTION

1. Field of the Invention

The present invention relates to a method for producing compounds having a double bond at an end of the molecule (hereinafter referred to as terminal olefin). More particularly, the invention relates to a method for producing terminal olefins by the dehydration of compounds represented by the general formula $$R-\underset{\underset{\text{OH}}{|}}{CH}-CH_3 \qquad (I)$$

wherein R is a $C_2$–$C_{20}$ hydrocarbon group having optionally double bonds.

2. Description of the Prior Art

Terminal olefins are very useful industrially as raw materials of heat-resistant polymers, comonomers constituting polyolefins, starting materials for producing detergents, and so forth.

It is known that olefins can be produced by the dehydration of compounds represented by formula (I) above. Details of this method can be known, for example, from J. Am. Chem. Soc., 85, 2180 (1968) and Oil Chemistry (Japan), 17, 236(1968).

However, the dehydration over the usual solid acid catalyst yields mainly internal olefins and the selective production of terminal olefins has been impossible in this way. While the dehydration catalyzed by zirconium oxide is also known, the selectivity of such simple zirconium oxide to terminal olefins is not always high but varies depending upon the nature of zirconium oxide used. Although thorium oxide is known as a catalyst for selective productions of terminal olefins, there are difficulties in the industrial use of thorium oxide as a catalyst since thorium, a radioactive element, gives rise to serious problems of safety.

SUMMARY OF THE INVENTION

To overcome such drawbacks of the hitherto known catalysts, the present inventors made intensive studies, which have resulted in finding that the use of a zirconium oxide catalyst treated with alkali solution for the dehydration elevates preferentially the yield of an intended terminal olefin to a large extent. Based on this finding, the present invention has been accomplished.

According to the present invention, there is provided a method for producing a compound having a double bond at an end of the molecule, comprising dehydrating a compound represented by the general formula $$R-\underset{\underset{\text{OH}}{|}}{CH}-CH_3 \qquad (I)$$

wherein R is a $C_2$–$C_{20}$ hydrocarbon group having optionally double bonds, in the presence of a zirconium oxide catalyst treated with alkali solution.

Thus, the present invention overcomes such drawbacks of the hitherto known catalysts that main products of the dehydration over these catalysts are internal olefins, viz. selectivities thereof are low for terminal olefins, and provides a method by which an intended terminal olefin can be produced highly selectively.

DETAILED DESCRIPTION OF THE INVENTION

The starting material used in the method of the present invention is a compound represented by the general formula $$R-\underset{\underset{\text{OH}}{|}}{CH}-CH_3 \qquad (I)$$

wherein R is any of $C_2$–$C_{20}$ hydrocarbon groups, which may have double bonds but are preferably $C_2$–$C_{10}$ hydrocarbon groups, more preferably $C_2$–$C_{10}$ saturated hydrocarbon groups. When the present invention is carried out by using such a starting material, a terminal olefin is selectively produced through the elimination of both the hydroxyl and a hydrogen of the methyl shown in Formula (I), forming water.

Examples of the compound represented by formula (1) include 1-cyclohexylethanol and 4-methyl-2-pentanol.

Suitable alkaline compounds for use in the alkali solution to treat the zirconium oxide catalyst in the present invention include, for example, hydroxides, carbonates, acetates, and acetylacetonates of alkali metals (Li, Na, K, Rb, Cs, and Fr), alkaline earth metals (Be, Mg, Ca, Sr, Ba, and Ra) and lantanoids (La, Ce, Pr, Nd, Pm, Sm, Eu, Gd, Tb, Dy, Ho, Er, Tm, Yb, and Lu) and organic amines (alkylamines, pyridine, and aniline). Of these compounds, preferred are hydroxides and carbonates of Na, K, Cs, Ca and Sr and particularly preferred are hydroxides of Na and K.

Suitable solvents for the alkali solution are water and organic solvents, e.g. methanol, ethanol, acetone, acetonitrile, hexane, and benzene.

In making up the alkali solution, a non-metal salt such as ammonium carbonate may be dissolved simultaneously for the purpose of facilitating the solution of metal salt. Suitable alkali concentrations are 0.001 to 80%, preferably 0.01 to 10%, by weight. Zirconium oxide as such or supported by a suitable carrier is treated with the solution made up as stated above. There is no particular restriction on the choice of zirconium oxide, but preferred is one free of much impurity metal elements and particularly preferred is one in which the total content of silicon dioxide and titanium dioxide is not more than 0.3% by weight.

The treatment of zirconium oxide is desirably carried out, for instance, as follows: Zirconium oxide is dipped in an alkali solution; an alkali solution is passed through a layer of zirconium oxide; or an alkali solution is sprayed on zirconium oxide. Then the alkali solution containing zirconium oxide is evaporated to dryness. The treatment time is usually from 0.1 to 100° hours, preferably from 1 to 30 hours. This catalyst is used normally after calcining at a temperature of 100° to 1500° C., preferably 300° to 1100° C., for a period of generally 0.1 to 50 hours, preferably 1 to 10 hours.

In the present invention, the dehydrating reaction is carried out as follows: While the mode of reaction is not particularly restricted, a fixed or fluidized catalyst bed/-vapor-phase reaction system is adopted. The reaction temperature is generally from 200° to 500° C., preferably from 300° to 400° C. The reaction pressure is also not particularly restricted; the reaction can be effected under atmospheric or slightly elevated pressure. If necessary, the vapor of feed compound (I) is diluted with an inert gas such as nitrogen gas before reaction. The reaction under reduced pressure also gives good results. The material feed rate expressed in LHSV is generally from 0.1 to 15 hr$^{-1}$, preferably from 0.5 to 5 hr$^{-1}$.

The following examples illustrate the present invention in more detail without limiting the scope of the invention.

tor was continuously supplied with 1-cyclohexylethanol at atmospheric pressure. Gas chromatographic analysis of the reactor effluent gas indicated that the reaction products were composed of a terminal olefin (vinylcyclohexane) and small amounts of an internal olefin (ethylidenecyclohexane) and a ketone (methyl cyclohexyl ketone). Conditions and results of the reaction are shown in Table 1.

TABLE 1

| Example | Concentration of alkali solution (wt %) | Reaction temperature (°C.) | LHSV (hr$^{-1}$) | Conversion (%) | Terminal olefin selectivity (%) | Internal olefin selectivity (%) | Ketone selectivity (%) |
| --- | --- | --- | --- | --- | --- | --- | --- |
| 2 | 0.05 | 380 | 2.1 | 95 | 91 | 4 | 5 |
| 3 | 0.5 | 381 | 2.4 | 90 | 92 | 1 | 7 |
| 4 | 2 | 379 | 2.1 | 91 | 91 | 2 | 7 |

EXAMPLE 1

A 10–24 mesh sieved fraction (15 ml) of zirconium oxide (hereinafter referred to as zirconia) was dipped for 20 hr in 190 ml of an aqueous solution containing 1 wt % of NaOH. This zirconia was then washed 12 times with 100 ml each of pure water, air-dried, and calcined in a nitrogen stream at 400° C. for 2 hr. Using the thus treated zirconia catalyst, dehydrating reaction was carried out as follows:

A hard glass tubular reactor (inner diameter 12.5 mm) having a tubular sheath (outer diameter 4 mm) for a thermocouple in the middle portion was filled with 4 ml of the alkali-treated zirconia catalyst, and externally heated in an electric furnace. This reactor was continuously supplied with a mixture of 2.3 ml/hr (LHSV=0.58 hr$^{-1}$) of 4-methyl-2-pentanol and 2 l/min of nitrogen gas at atmospheric pressure through a gasifier heated at 330° C. in an electric furnace. Gas chromatographic analysis of the reactor effluent gas indicated a conversion of 92% of fed 4-methyl-2-pentanol and selectivities to 4-methyl-1-pentene, 4-methyl-2pentene, and methyl isobutyl ketone of 85%, 3%, and 12%, respectively. The temperature of the electric furnace during this reaction was 327° C.

EXAMPLES 2–4

A 10–24 mesh sieved fraction (ml) of zirconia was dipped for 20 hr in 100 ml each of aqueous NaOH solutions of three different concentrations (0.05, 0.5, and 2 wt %). In each zirconia, contents of SiO$_2$ and TiO$_2$ were up to 0.02 wt % and up to 0.01 wt %, respectively. Each zirconia was then washed 8 times with 50 ml each of pure water, air-dried, and calcined in a nitrogen stream at 400° C. for 2 hr. Using the thus treated zirconia catalysts, dehydrating reaction was carried out as follows:

A stainless steel tubular reactor (inner diameter 4 mm) was filled with 8 ml of each alkali-treated catalyst, and externally heated in an electric furnace. This reac-

EXAMPLES 5–12

Experiments were made by using zirconia catalysts treated separately with solutions of different alkali compounds. The catalyst preparation and the reaction were conducted in the same manner as in Example 1. Each zirconia catalyst contained up to 0.02 wt % of SiO$_2$ and up to 0.01 wt % of TiO$_2$. 4-Methyl-2-pentanol was used as starting material. Thus, the reaction products were composed of a terminal olefin (4-methyl-1-pentene) and small amounts of an internal olefin (4-methyl-2-pentene) and a ketone (methyl isobutyl ketone). Conditions and results of the reaction are shown in Table 2.

TABLE 2

| Example | Alkali compound | Concentration of alkali solution (wt %) | Reaction temperature (°C.) | LHSV (hr$^{-1}$) | Conversion (%) | Terminal olefin selectivity (%) | Internal olefin selectivity (%) | Ketone selectivity (%) |
| --- | --- | --- | --- | --- | --- | --- | --- | --- |
| 5 | LiOH | 1 | 315 | 0.58 | 88 | 93 | 4 | 4 |
| 6 | NaOH | 1 | 315 | 0.58 | 88 | 93 | 4 | 3 |
| 7 | KOH | 1 | 310 | 0.58 | 92 | 94 | 3 | 3 |
| 8 | Cs$_2$CO$_3$ | 4.8 | 310 | 0.58 | 86 | 96 | 2 | 2 |
| 9 | MgCO$_3$ | 0.01 | 306 | 0.58 | 91 | 92 | 4 | 4 |
| 10 | Ca(OH)$_2$ | 0.13 | 315 | 0.58 | 90 | 94 | 2 | 4 |
| 11 | Sr(OH)$_2$ | 1.0 | 313 | 0.58 | 91 | 94 | 3 | 4 |
| 12 | Ba(OH)$_2$ | 4.5 | 320 | 0.58 | 91 | 93 | 2 | 5 |

EXAMPLE 13

An experiment was made according to the procedure of Examples 2–4 except that a 2%(wt) aqueous KOH solution was used in place of the aqueous NaOH solution for treating zirconia, the reaction temperature was kept at 378° C. and 1-cyclohexylethanol was fed at an LHSV of 3.6 hr$^{-1}$.

The conversion of fed 1-cyclohexylethanol was 94% and selectivities to vinylcyclohexane, ethylidenecyclohexane, and methyl cyclohexyl ketone were 92%, 2%, and 6%, respectively.

COMPARATIVE EXAMPLE 1

4-Methyl-2-pentanol was reacted to dehydrate in the same manner as in Example 1 except that zirconia was used without alkali treatment and the electric furnace temperature during the reaction was kept at 321° C.

The conversion of fed 4-methyl-2-pentanol was 86% and selectivities to 4-methyl-1-pentene, 4-methyl-2pentene, and methyl isobutyl ketone were 60%, 30%, and 4%, respectively.

COMPARATIVE EXAMPLE 2

1-Cyclohexylethanol was reacted to dehydrate in the same manner as in Examples 2–4 except that the same zirconia as prepared in Examples 2–4 and 13 was used without alkali treatment, the reaction temperature was kept at 359° C., and 1-cyclohexylethanol was fed at a rate of 28 ml/hr (LHSV=3.5 hr$^{-1}$).

The conversion of fed 1-cyclohexylethanol was 77% and selectivities to vinylcyclohexane, ethylidene cyclohexane, and methyl cyclohexyl ketone were 60%, 27%, and 6%, respectively.

COMPARATIVE EXAMPLE 3

4-Methyl-2-pentanol was reacted to dehydrate in the same manner as in Example 1 except that the same zirconia as prepared in Examples 5–12 was used without alkali treatment and the reaction temperature was kept at 301° C.

The conversion of fed 4-methyl-2-pentanol was 8% and selectivities to 4-methyl-1-pentene, 4-methyl-2-pentene, and methyl isobutyl ketone were 85%, 7%, and 4%, respectively.

EXAMPLE 14

A 10–24 mesh sieved fraction (15 ml) of zirconia was dipped for 20 hr in 190 ml of a methanolic solution containing 1 wt % of NaOH. This zirconia was then washed 12 times with 100 ml each of pure water, air-dried, and calcined in a nitrogen stream at 400° C. for 2 hr. Using the thus treated zirconia catalyst, 4-methyl-2-pentanol was reacted to dehydrate in the same manner as in Example 1 except that the reaction temperature was kept at 320° C. and 4-methyl-2-pentanol was fed at an LHSV OF 0.58 hr$^{-1}$.

The conversion of fed 4-methyl-1-pentanol was 90% and selectivities to 4-methyl-1-pentene, 4-methyl-2pentene, and methyl isobutyl ketone were 92%, 3%, and 5%, respectively.

As has been described hereinbefore, a terminal olefin can be produced in markedly high selectivity according to the present invention by the dehydrating reaction of a compound represented by formula (I) in the presence of a zirconium oxide catalyst treated with alkali solution. Thus the invention is of great industrial value.

What is claimed is:

1. A method for producing a compound having a double bond at an end of the molecule, comprising dehydrating a compound represented by the general formula $$R-\underset{\underset{\displaystyle}{|}}{\overset{\overset{\displaystyle OH}{|}}{CH}}-CH_3 \qquad (I)$$

wherein R is a $C_2$–$C_{20}$ hydrocarbon group having optionally double bonds, in the presence of a zirconium oxide catalyst treated with alkali solution.

2. The method of claim 1, wherein the catalyst is one prepared by alkali-solution treatment of high purity zirconium oxide in which the total content of silicon and titanium is up to 0.3% by weight in terms of their dioxides.

3. The method of claim 1, wherein the alkali is a hydroxide, carbonate, or acetate of an alkali metal or alkaline earth metal.

4. The method of claim 1, wherein the alkali is sodium hydroxide or potassium hydroxide.

5. The method of claim 1, wherein the alkali concentration in the alkali solution is from 0.001 to 80% by weight.

6. The method of claim 1, wherein the solvent of the alkali solution is water, an alcohol or a mixture thereof.

7. The method of claim 1, wherein R in the general formula (I) is a $C_3$–$C_{20}$ hydrocarbon group.

8. The method of claim 1, wherein the compound represented by the general formula (I) is 1-cyclohexylethanol or 4-methyl-2-pentanol.

9. The method of claim 1, wherein the reaction temperature is between 200° C. and 500° C.

10. The method of claim 1, wherein the treatment of zirconium oxide with alkali solution is performed by dipping the oxide in an alkali solution or passing an alkali solution through a layer of the oxide.

11. The method of claim 1, wherein the zirconium oxide catalyst treated with alkali solution is used after calcined at a temperature of 100° to 1500° C. for a period of 0.1 to 50 hours.

* * * * *